(12) United States Patent
Goldberg et al.

(10) Patent No.: US 12,121,672 B2
(45) Date of Patent: Oct. 22, 2024

(54) ADVANCED SHEATH PATTERNS

(71) Applicant: Edwards Lifesciences Corporation, Irvine, CA (US)

(72) Inventors: Eran Goldberg, Nesher (IL); Liron Tayeb, Peduel (IL); David Maimon, Atlit (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 972 days.

(21) Appl. No.: 17/078,556

(22) Filed: Oct. 23, 2020

(65) Prior Publication Data

US 2021/0052849 A1   Feb. 25, 2021

Related U.S. Application Data

(63) Continuation of application No. PCT/US2019/028833, filed on Apr. 24, 2019.

(60) Provisional application No. 62/664,831, filed on Apr. 30, 2018.

(51) Int. Cl.
| | |
|---|---|
| *A61F 2/24* | (2006.01) |
| *A61M 25/00* | (2006.01) |
| *A61F 2/962* | (2013.01) |

(52) U.S. Cl.
CPC ....... *A61M 25/0023* (2013.01); *A61F 2/2427* (2013.01); *A61F 2/962* (2013.01); *A61M 2025/0024* (2013.01)

(58) Field of Classification Search
CPC ............ A61M 25/0023; A61M 25/005; A61M 2025/0024; A61F 2/2427; A61F 2/962; A61F 2/95; A61B 17/22
See application file for complete search history.

(56) References Cited

U.S. PATENT DOCUMENTS

| | | |
|---|---|---|
| 519,297 A | 5/1894 | Bauer |
| 4,035,849 A | 7/1977 | Angell et al. |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Erich G Herbermann
(74) *Attorney, Agent, or Firm* — Meunier Carlin Curfman LLC; Joel B. German

(57) ABSTRACT

Disclosed herein are reinforced expandable introducer sheaths and methods of using the same. The sheaths minimize trauma to the patient's vasculature by including a reinforcing member to improve the push force of the sheath while reducing the chances of kinking during delivery of a prosthetic device. The sheath can include a plurality of expandable rings aligned along the longitudinal axis of the sheath and coupled together to form an elongated tubular structure. The sheath can also include a plurality of radial members circumferentially arranged to form a tubular support structure. The radial members slidingly interconnected around the circumference of the tubular structure to facilitate radial expansion of the sheath.

13 Claims, 13 Drawing Sheets

(56) References Cited

U.S. PATENT DOCUMENTS

| | | |
|---|---|---|
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,537,311 B1* | 3/2003 | Cox .................. A61F 2/91 623/1.15 |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 10,548,631 B2* | 2/2020 | Fitterer ............... A61B 17/3431 |
| 11,033,714 B2* | 6/2021 | Schultz ............... A61B 18/1492 |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0069424 A1* | 3/2006 | Acosta ............... A61F 2/91 623/1.12 |
| 2006/0264904 A1* | 11/2006 | Kerby ............... A61M 25/0043 604/523 |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0103520 A1 | 5/2008 | Selkee |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |
| 2013/0030519 A1 | 1/2013 | Tran et al. |

(56) References Cited

U.S. PATENT DOCUMENTS

| | | | |
|---|---|---|---|
| 2013/0281787 A1* | 10/2013 | Avneri | A61B 17/12109 604/528 |
| 2013/0317598 A1 | 11/2013 | Rowe et al. | |
| 2014/0277079 A1* | 9/2014 | Vale | A61B 17/221 606/200 |
| 2014/0296962 A1 | 10/2014 | Cartledge et al. | |
| 2017/0065415 A1 | 3/2017 | Rupp et al. | |
| 2018/0001058 A1* | 1/2018 | Schlesinger | A61B 34/74 |
| 2018/0153689 A1 | 6/2018 | Maimon et al. | |
| 2018/0344456 A1 | 12/2018 | Barash et al. | |

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

\* cited by examiner

ADVANCED SHEATH PATTERNS

CROSS-REFERENCE TO RELATED APPLICATION

This application is a continuation of pending International Application No. PCT/US2019/028833, filed Apr. 24, 2019, which claims priority to and the benefit of U.S. Provisional Patent Application No. 62/664,831, filed Apr. 30, 2018 and entitled "Advanced Sheath Patterns." Each of the aforementioned applications is hereby incorporated by reference herein in its entirety.

TECHNICAL FIELD

The present application is directed to an expandable sheath for use with catheter-based technologies to introduce a prosthetic device, such as a heart valve or other implant, into the patient's vasculature.

BACKGROUND

Endovascular delivery catheter assemblies are used to implant prosthetic devices, such as a prosthetic heart valve, at locations inside the body that are not readily accessible by surgery or where less invasive surgery is desirable. For example, aortic, mitral, tricuspid, and/or pulmonary prosthetic valves can be delivered to a treatment site using minimally invasive surgical techniques, including transcatheter delivery methods.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for the prosthetic implant, such as a heart valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel during insertion and removal of the sheath.

Radially expanding intravascular sheaths reduce the overall profile of the sheath to reduce risk of damage to the vessel. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque. The addition of radially expanding properties can also hinder a practitioner's ability to push the sheath without it bending or kinking. Thus, there remains a need for further improvements in introducer sheaths for endovascular systems used for implanting heart valves and other prosthetic devices.

SUMMARY

Disclosed here are expandable introducer sheaths and methods of making and using the same. The expandable introducer sheath disclosed herein are used to deliver a prosthetic device through a patient's vasculature to a procedure site within the body. The sheath is constructed to be highly expandable and collapsible in the circumferential direction, while also minimizing the wall thickness of the sheath to minimize the profile of the delivery system. The sheaths are adapted to temporarily expand a portion of the sheath to allow for the passage of a delivery system for a cardiovascular device, then return to a non-expanded state after the passage of the system. In addition, the sheath disclosed herein includes a plurality of radially expandable rings aligned along the longitudinal axis of the sheath. The expandable rings facilitate radial expansion while maintaining the overall length of the sheath.

Some embodiments include an expandable sheath having at least two expandable rings. The rings each include longitudinally extending beams spaced circumferentially around the ring and an expandable strut extending between each of the beams. The expandable rings aligned along the longitudinal axis of the sheath and coupled together along a coupling member passing through each of the expandable rings to form an elongated tubular structure. Each of the expandable rings expand radially between a non-expanded and expanded state.

In some embodiments, each of the expandable rings have a height (H) between 5.0 mm and 6.5 mm measured along the longitudinal axis of the sheath. In some embodiments, at least one of the beams on each of the expandable rings include a throughbore, where the coupling member extends through the throughbore. In some embodiments, the beams of each of the expandable rings include a throughbore, and a coupling member extends through each of the throughbores. The coupling member includes at least one of a wire, a braided cable, and a polymer suture.

In some embodiments, a beam on each of the expandable rings includes a proximal end mating feature at a proximal end of the beam and a distal end mating feature at a distal end of the beam, where the proximal end mating feature is sized and configured to engage the corresponding distal end mating feature of a longitudinally adjacent beam. In some embodiments, the beams on each of the rings include a proximal end mating feature at a proximal end of the beam and a corresponding distal end mating feature at a distal end of the beam, where the proximal end mating features are sized and configured to engage the corresponding distal end mating features of longitudinally adjacent beams.

In some embodiments, the expandable strut on each of the rings expands circumferentially between the non-expanded and the expanded state such that the circumferential distance between adjacent beams of the corresponding ring increases during expansion. In some embodiments, the expandable strut on each of the rings elastically deforms during expansion. In some embodiments, one of the expandable rings is constructed from a material having a stiffness greater than a stiffness of another one of the expandable rings. In some embodiments, in the non-expanded state, the expandable strut on each of the rings is coupled to the corresponding longitudinally extending beam at an acute angle and defines a generally "V" shape. In some embodiments, the overall length of the elongated tubular (support) structure remains constant between the expanded and the non-expanded state.

In some embodiments, the expandable rings are coupled to an expandable inner tubular member. An elastic outer member extends over the inner tubular member, the elastic outer member comprising a material having an elastic modulus greater than an elastic modulus of the inner tubular member.

In some embodiments, the expandable rings are encased within an expandable material. An elastic outer member extends over the encased expandable rings, the elastic outer member comprising a material having an elastic modulus greater than an elastic modulus of the expandable material.

Further disclosed herein is an expandable sheath including a plurality of elongated radial members circumferentially arranged to define the tubular form of the support structure of the sheath. Each of the elongated radial members is slidably interconnected to an adjacent member to facilitate radial expansion of the support structure and the sheath. In some embodiments, the expandable sheath includes a plurality of elongated radial members slidably interconnected to form a tubular structure. Each of the radial members includes a locking arm having a locking projection extending from an end of the locking arm and a retaining portion having a central channel sized and configured to accommodate sliding engagement of a locking arm and locking projection of an adjacent elongated radial member. The radial members are circumferentially arranged such that the locking arm of each of the radial members slidably engages a corresponding retaining portion of an adjacent radial member. The radial members move between a non-expanded and expanded state where the circumference of the tubular structure formed by the radial members is greater in the expanded state than the circumference of the tubular structure in the non-expanded state.

In some embodiments, movement of the plurality of radial members between the non-expanded and expanded state causes the locking arms of each of the plurality of elongated radial members to move circumferentially within the central channel of the retaining portion of an adjacent radial member. In some embodiments, each of the plurality of radial members define an arcuate shape in cross-section.

In some embodiments, each of the retaining portions include an entrance opening having an engagement member sized and configured to retain the locking projection of an adjacent radial member. The engagement member of each of the retaining portions extends in a direction towards the central channel of the respective retaining portion.

In some embodiments, the locking projection cannot be removed from the corresponding retaining portion of an adjacent radial member without fatally deforming either the locking arm or the corresponding retaining portion. In some embodiments, an expandable inner tubular member extends over the plurality of radial members. An elastic outer member extends over the inner tubular member, the elastic outer member comprising a material having an elastic modulus greater than an elastic modulus of the inner tubular member.

DESCRIPTION OF DRAWINGS

Like reference symbols in the various drawings indicate like elements.

DETAILED DESCRIPTION

Figure 1:
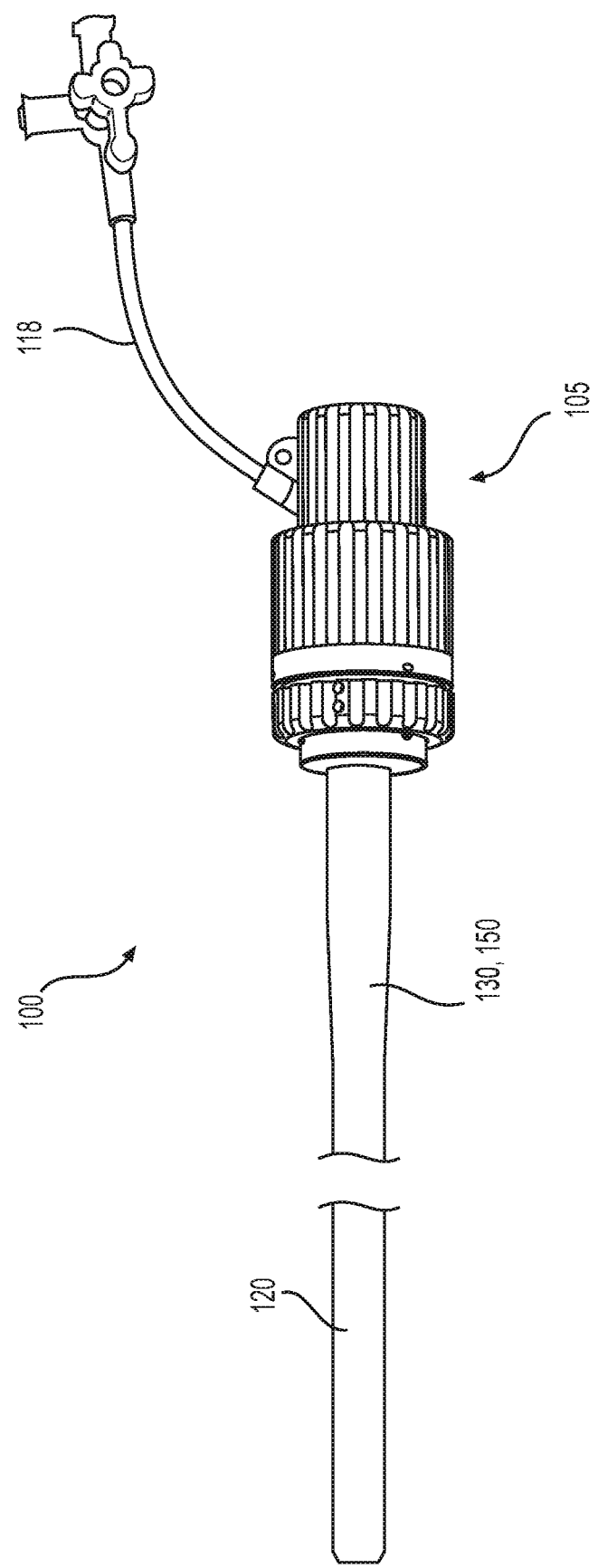
FIG. 1 is a side view of an example introducer sheath.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device. "Axially" or "axial" as used herein refers to a direction along the longitudinal axis of the sheath.

The term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

The expandable introducer sheath disclosed herein is used to deliver a prosthetic device through a patient's vasculature to a procedure site within the body. As will be described in further detail below, the sheath is constructed to be highly expandable and collapsible in the circumferential direction, while also minimizing the wall thickness of the sheath to minimize the profile of the delivery system during delivery. In one example, the expandable sheath includes a plurality of radially expandable rings aligned along the longitudinal axis of the sheath. The expandable rings provide a tubular support structure that facilitates radial expansion of the sheath while maintaining the overall length of the sheath. In another example, the sheath includes a plurality of elongated radial members circumferentially arranged to define a tubular support structure. Each of the elongated radial members is slidably interconnected to an adjacent member to facilitate maximum radial expansion of the sheath while maintaining the sheath length.

FIG. 1 illustrates an introducer sheath system 100 according to the present disclosure. As will be described below, the introducer sheath system 100 is configured for use with a delivery apparatus 200 (FIG. 2) for delivering a prosthetic implant, such as a prosthetic heart valve, to a patient. For example, in use, the shaft 222 of the guide catheter 214 of the representative delivery apparatus 200, shown in FIG. 2, is inserted through the handle 105 and sheath 120 of the introducer sheath system 100, shown in FIG. 1, to deliver a prosthetic device to a patient.

As illustrated in FIG. 1, the sheath 120 of the introducer sheath system 100 includes an outer tubular member 150 and an inner tubular member 130 (not visible in FIG. 1), where the outer tubular member 150 provides an elastic layer that extends over the inner tubular member 130. The outer member 150 can be formed of an elastomeric material, such as silicone or urethane, for example. An elastomeric outer tubular member 150 will stretch to conform to the expansion state of the underlying structure. The introducer sheath system 100 includes a handle 105 provided at the proximal end of the sheath 120. In use, delivery apparatus 200 is inserted through a central lumen extending through both the handle 105 and the sheath 120 for delivering the prosthetic implant. A hemostasis valve is included at the proximal end of the central lumen that prevents leakage of pressurized blood out of the introducer sheath system 100.

Figure 2:
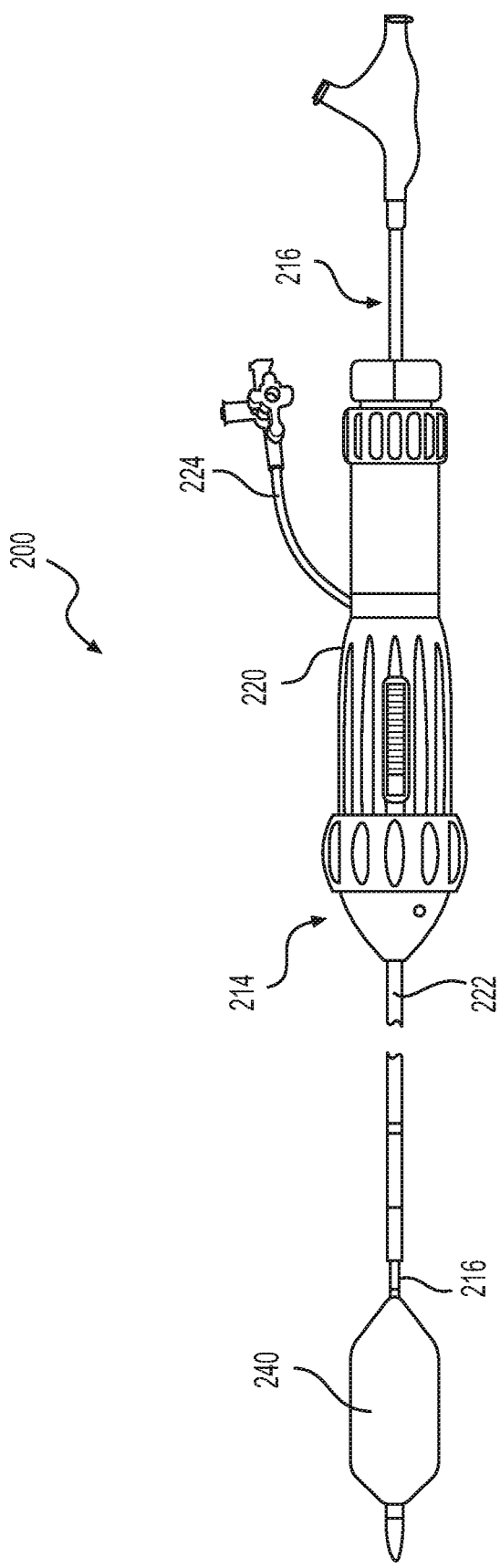
FIG. 2 is a side view of an example endovascular delivery apparatus for implanting a prosthetic valve.

FIG. 2 illustrates a representative delivery apparatus 200. The delivery apparatus 200 described herein is exemplary only, other similar delivery systems can be used with the introducer sheath system 100. The delivery apparatus 200 illustrated in FIG. 2 includes a steerable guide catheter 214 comprising a handle portion 220 coupled to an elongated shaft 222. A balloon catheter 216 extends through the handle portion 220 and the elongated shaft 222 of the guide catheter 214, and is in fluid communication with balloon 240. The guide catheter 214 and the balloon catheter 216 illustrated in FIG. 2 are adapted to slide longitudinally relative to each other to facilitate delivery and positioning of a prosthetic heart valve at an implantation site in a patient's body. In FIG. 2, balloon 240 is depicted in an inflated state, but it is understood that balloon 240 is deflated during advancement through the introducer sheath system 100 and the patient's vasculature. A prosthetic heart valve or other prosthetic device can be crimped onto balloon 240 for delivery to the procedure site. The delivery apparatus 200 also includes flush tubing 224 to prevent air bubbles from entering the bloodstream.

Generally, before insertion, the sheath 120 is coupled with an introducer, which inserted through the central lumen and used to rigidify the sheath to prevent collapse during insertion into the patient. The distal end of the sheath 120 is passed through the skin of the patient and into a vessel, such as the femoral artery. The shaft 222 of the guide catheter 214 is then inserted into the introducer sheath system 100 through the proximal hemostasis valve. The shaft 222 of the delivery apparatus 200 is advanced through the patient's vasculature to deliver the prosthetic device to the patient. Flush tubing 118 is attached to the introducer sheath system 100 and is used to fill the system with saline or another physiologically balanced solution prior to advancing the sheath 120 into the patient, to ensure no air bubbles are introduced to the bloodstream.

FIGS. 3-21 illustrate various example support structures 300 included in the introducer sheath 120 for use with a delivery apparatus 200, such as that shown in FIG. 2. The sheath 120 is adapted to allow for temporary (local) radial expansion of a portion of the sheath 120 to accommodate passage of the delivery apparatus 200 through the central lumen of the sheath 120 and into a patient's vessel to deliver, remove, repair, and/or replace a prosthetic device. Such introducer sheaths 120 can also be useful for other types of minimally invasive surgery, such as any surgery requiring introduction of an apparatus into a subject's vessel. For example, the sheath 120 can also can be used to introduce other types of delivery apparatus for placing various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

The sheath 120 can include various support structures 300 to radially and axially support the sheath 120 during advancement through the patient and passage of the delivery apparatus 200, and to prevent bending or kinking of the sheath 120 during advancement into the patient. The support structure 300 also facilitates temporary (local) radial expansion of a portion of the sheath 120 to accommodate passage of the delivery apparatus 200 and delivery of the prosthetic device. The support structure 300 can be coupled to an inner or outer surface of the inner tubular member 130 or encased within the inner tubular member 130. Any form of mechanical or chemical fastener for coupling the support structure 300 to the inner tubular member 130 is contemplated. For example, the support structure 300 can be chemically bonded to the interior surface of the inner tubular member 130 using an adhesive. In another example, the support structure 300 can be mechanically coupled to the inner tubular member 130 using a suture, thread, wire, rivet, screw, pin, or similar element. While the support structure 300 is described herein as coupled to the inner tubular member 130, it is contemplated that the support structure 300 can be coupled to either (or both) the inner tubular member 130 and outer tubular member 150 using similar coupling/fastening mechanisms.

The support structure 300 can be constructed from a material having a stiffness greater than the inner and outer tubular members 130, 150. For example, the support structure 300 can be constructed from any biocompatible material including, but not limited to, composites, polymers, reinforced polymers, and metals such as stainless steel, titanium, titanium alloys, cobalt chromium, Nitinol, etc. Accordingly, the support structure 300 increases the push/pull force of the sheath 120 while also preventing kinking upon advancement of the delivery apparatus 200 and the prosthetic device. The combination of the support structure 300 with the expandable inner tubular member 130 provides a sheath 120 that has high push/pull force while at the same time is soft and flexible, and capable of expanding radially.

Figure 3:
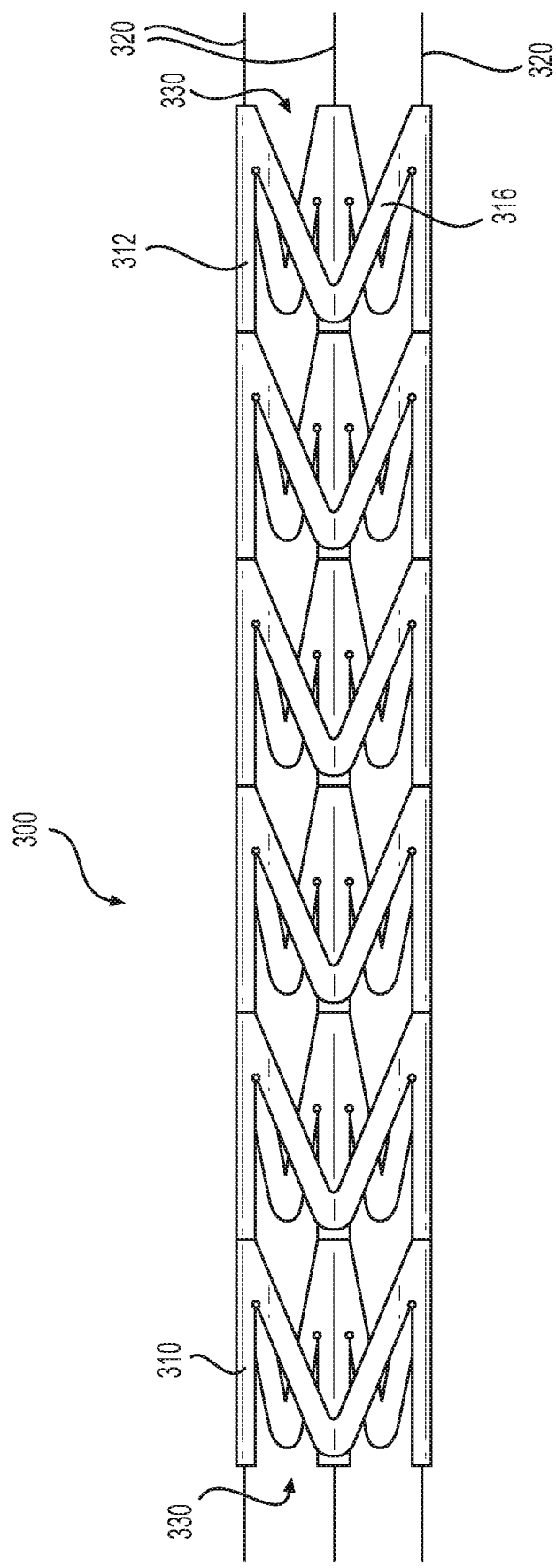
FIG. 3 is a side view of an example support structure.
Figure 4:
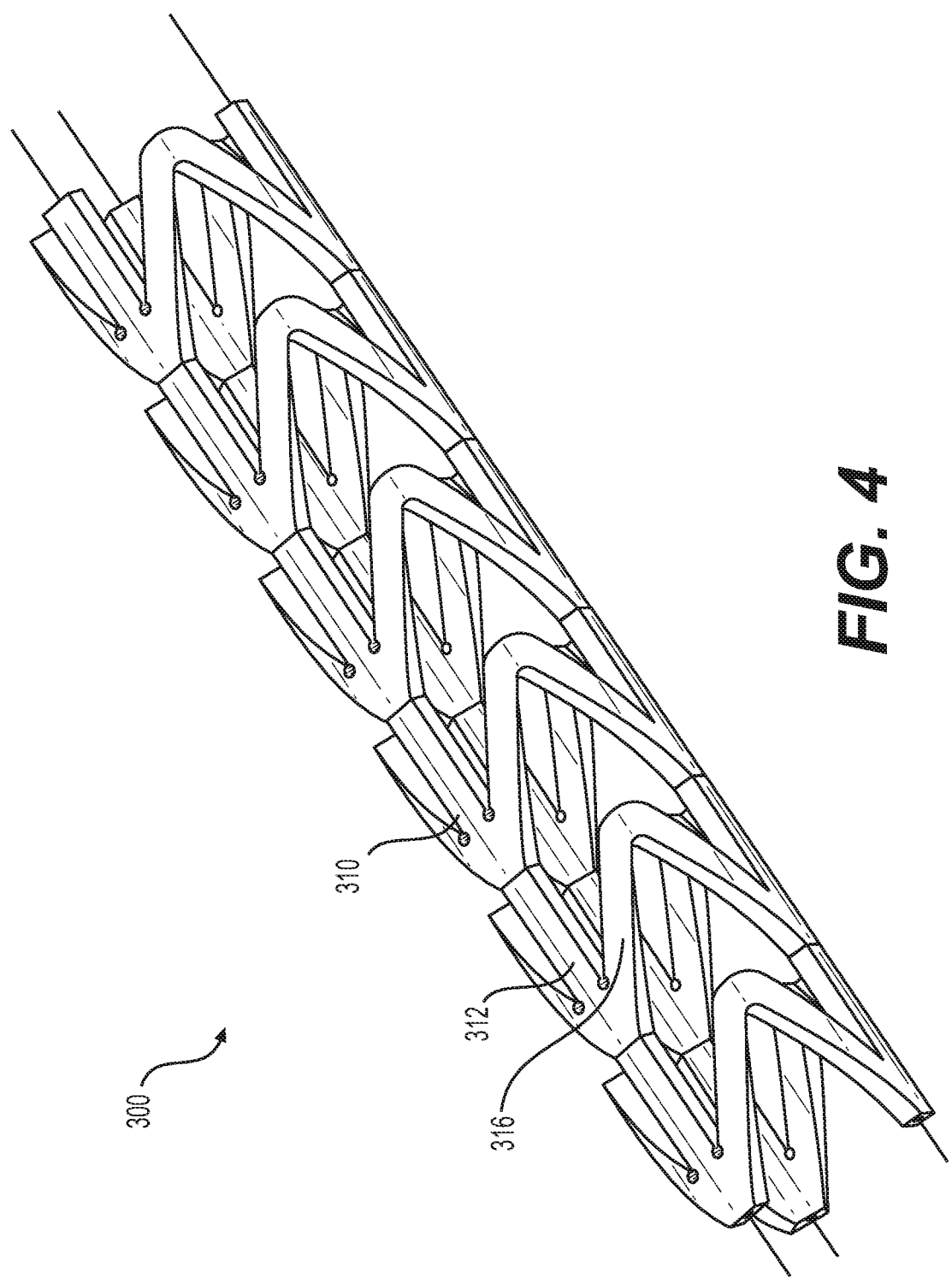
FIG. 4 is a perspective view of the support structure of FIG. 3.

FIGS. 3 and 4 illustrate an example support structure 300 including a plurality of radially expandable rings 310. The adjacent rings 310 are coupled together and axially aligned along the longitudinal axis of the inner tubular member 130/sheath 120. The resulting tubular structure has a generally uniform thickness in the circumferential direction and a length defined by the combined height of the coupled rings 310. The support structure 300 defines a central lumen 330 to allow passage of the delivery apparatus 200 and delivery of the prosthetic device through the support structure 300/inner tubular member 130. As will be described below, the expandable rings 310 expand radially between a non-expanded and expanded state to facilitate radial expansion of the inner tubular member 130/sheath 120 while maintaining the overall length of the sheath 120 and support structure 300.

While the portion of the support structure 300 illustrated in FIGS. 3 and 4 includes only six expandable rings 310, it is contemplated that a support structure 300 can include more than six radially expandable rings 310. Each of the radially expandable rings 310 can have a height (H) of about 1.0 mm to 10.0 mm. In a further example, each of the radially expandable rings 310 can have a height (H) of about 5.0 mm to about 20 mm. In yet a further example, each of the radially expandable rings 310 can have a height (H) of about 2.0 mm to about 20 mm. Accordingly, an example support structure 300 coupled along an entire length of the inner tubular member 130 will have more than 25 radially expandable rings 310. The number of radially expandable rings 310 included in the support structure 300 can be adjusted according to the procedure being performed, patient anatomy, desired flexibility of the support structure 300, and/or desired expansion rate of the support structure 300. For example, the support structure 300 can be coupled to a portion of the length of the inner tubular member 130, where the number of radially expandable rings 310 used corresponds to the desired length of the support structure 300.

The radially expandable rings 310 are axially aligned along the longitudinal axis of the inner tubular member 130/sheath 120. The rings 310 are coupled together along a coupling member 320 passing through each of the plurality of expandable rings 310. The coupling member 320 can include a wire, a braided cable, and/or a polymer suture. Example coupling members 320 include a polymer or metal wire, a composite braided cable, or a polymer suture constructed from Dyneema. Sufficient tension is provided on the coupling member 320 to maintain the axial/longitudinal position of the expandable rings 310 along support structure 300 and the inner tubular member 130. Additionally, sufficient tension is provided on the coupling member 320 to maintain the expandable rings 310 in an immediately adjacent/abutting configuration to minimize any axial movement or gap between adjacent expandable rings 310.

As provided in FIGS. 3 and 4, when coupled, the radially expandable rings 310 form an elongated tubular support structure 300. As the delivery apparatus 200 passes through the central lumen 330 of the support structure 300 (and inner tubular member 130), each of the radially expandable rings 310 will individually expand in a radially direction from a non-expanded to an expanded state. For example, as the delivery apparatus 200 passes through the central lumen 330 of the support structure 300, the prosthetic device and the delivery apparatus 200 exert a radially outward directed force on the adjacent radially expandable rings 310. The radially expandable rings 310 exert a corresponding radially outward directed force on the inner tubular member 130 and the elastic outer tubular member 150, causing both the inner and outer tubular members 130, 150 to locally expand to accommodate the profile of the prosthetic device/delivery apparatus 200. Once the prosthetic device/delivery apparatus 200 has passed, the expandable rings 310 individually recover toward the non-expanded diameter. That is, the expandable rings 310, and inner and outer tubular members 130, 150, return to their original, non-expanded configuration. In some embodiments, this is facilitated by the outer tubular member 150 having a higher elastic modulus than inner tubular member 130. In this configuration, the outer tubular member 150 urges the inner tubular member 130 back towards its non-expanded configuration. If desired, a lubricious liner can be provided within the central lumen 330 to reduce friction between the passing delivery apparatus 200/prosthetic device and support structure 300. Examples of suitable lubricious liners can be constructed from materials such as PTFE, polyethylene, polyvinylidine fluoride, and combinations thereof.

Figure 5:
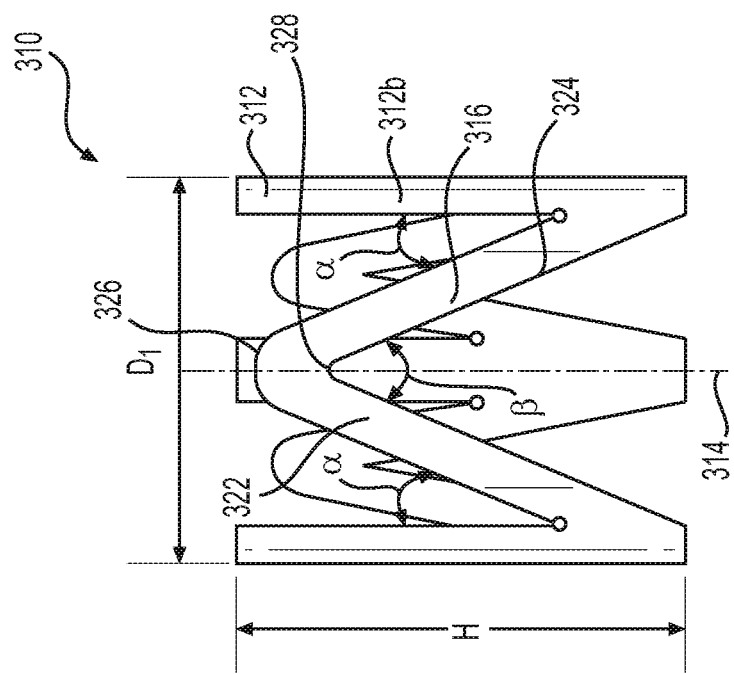
FIG. 5 is a front view of an expandable ring in a non-expanded configuration.

FIG. 5 provides a side view of a single radially expandable ring 310 in a non-expanded state. The expandable ring 310 includes several longitudinally extending beams 312 spaced circumferentially around the expandable ring 310. The beams 312 extend in a direction parallel to the longitudinal axis 314 of the expandable ring 310, and the inner tubular member 130. Struts 316 extend between and connect each of the beams 312. As illustrated in FIG. 5 (and FIG. 9), the struts 316 define a generally "V" shape. The struts 316 includes a first leg 322 and a second leg 324 extending at acute angles ($\alpha$) from the adjacent beams 312$a$ and 312$b$. The first and second legs 322, 324 meet at an apex 326 such that an acute angle ($\beta$) is defined between the legs 322, 324. Other shapes and patterns for the struts 316 are contemplated. For example, the struts 316 can also define a generally "U" shape, a generally "W" shape, or any other regular or irregular shape connecting adjacent beams 312 that facilitates radial expansion of the expandable ring 310. As illustrated in FIG. 5, the apex 326 of the strut 316 has a (non-expanded) height corresponding to the height (H) of the beams 312. Though not illustrated, it is contemplated that the apex 326 may have a (non-expanded) height less than or greater than the height (H) of the beams 312. In one embodiment, the apex 326 of the strut 316 is oriented towards the distal end of the support structure 300/inner tubular member 130. In another embodiment, the apex 326 of the strut 316 is orientated towards the proximal end of the support structure 300/inner tubular member 130. In a further embodiment, the apexes 326 of adjacent expandable rings 310 alternate in orientation with respect to the proximal or distal end of the support structure 300/inner tubular member 130.

Figure 6:
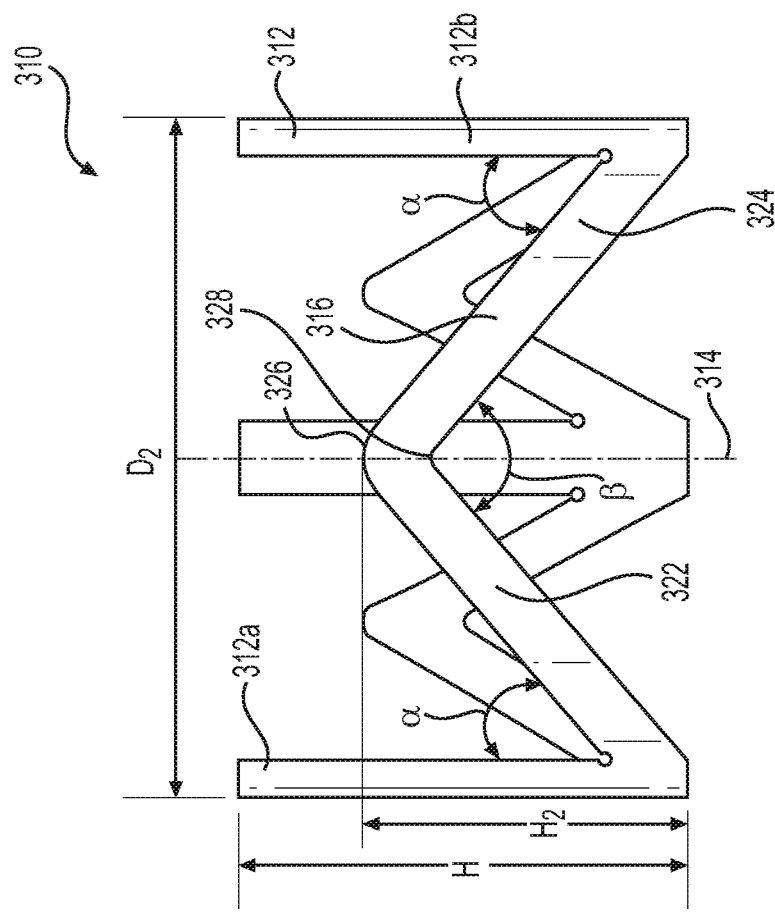
FIG. 6 is a front view of the expandable ring of FIG. 5 in an expanded configuration.

FIG. 6 provides a side view of the expandable ring 310 of FIG. 5 in an expanded state. As illustrated in FIGS. 5 and 6, the diameter of the expandable ring 310 increases between the non-expanded diameter ($D_1$) and expanded diameter ($D_2$). During expansion, the struts 316 expand circumferentially between the non-expanded and the expanded state such that the circumferential distance (arc length) between adjacent beams 312 increases as the diameter of the expandable ring 310 increases. In some embodiments, the struts 316 elastically deform when the expandable ring 310 is moved between the expanded and non-expanded state. For example, the struts 316 temporarily change shape under the force of the passing prosthetic device/delivery apparatus 200 and return to their original shape once the device/apparatus has passed. As illustrated in FIG. 6, the struts 316 are shown having flexed, moved, and/or elongated circumferentially around the perimeter of the expanded ring 310 such that the angle ($\alpha$) between the legs 322, 324 and the adjacent beams 312$a$, 312$b$ has increased, the angle ($\beta$) between the legs 322, 324 has increased, and the height ($H_2$) of the apex 326 of the strut 316 has decreased. Once the prosthetic device/delivery apparatus 200 has passed through the expandable ring 310, the strut 316 will return to its original, non-expanded configuration.

As illustrated in FIGS. 5 and 6, while the circumferential distance between the beams 312 increases, the height (H) of the expandable ring 310 and beams 312 does not change during expansion. Because the longitudinal beams 312 do not flex or bend during expansion, height (H) of the beams 312 remains constant, and the overall length of the support structure 300 and inner tubular member 130 remains constant.

As outlined above, the expandable rings 310 of the support structure 300 can be constructed from any biocompatible material including composites, polymers such as PEEK (polyether ether ketone), POM (polyoxymethylene, such as DELRIN by DuPont), or other reinforced polymers like PARA (polyacrylamide, such as IXEF by Solvay), and metals (e.g., stainless steel, titanium, titanium alloys, cobalt chromium, Nitinol), and other similar materials capable of elastic deformation. While the struts 316 are generally described as constructed from an elastically deformable material, the struts 316 and/or beams 312 can also be constructed from a material capable of plastic deformation. In these embodiments, the support structure 300 will maintain its expanded shape upon expansion.

While each of the expandable rings 310 included in the example support structure 300 can be constructed from the same material, it is contemplated that various rings 310 within the support structure 300 can be constructed from different materials. For example, at least one of the plurality of expandable rings 310 can be constructed from a material having a stiffness greater or less than the stiffness of remaining expandable rings 310. Given that rings 310 constructed from a stiffer material provide more resistance to expansion and rings 310 constructed from a more flexible material will generally flex more (and more quickly), by providing expandable rings 310 of varying stiffness/flexibility the rate and amount of expansion of various portions of the support structure 300 can be controlled. It is also contemplated that different components of the expandable ring 310 can be constructed from different materials. For example, within a given expandable ring 310, the beams 312 can be constructed from a different material than the struts 316. In one example, the struts 316 can be constructed from a material with high elastic flexibility to promote radial movement between the expanded and non-expanded configurations, and the beams 312 can be constructed from a stiffer material increasing the push/pull strength of the support structure 300/sheath 120. It is also contemplated that expandable rings 310 having different height (H) can be provided along the same support structure 300. Likewise, expandable rings 310 having different strut 316 shape (V-shape, U-shape, etc.) can be provided along the same support structure 300. By varying materials (both between rings 310 and among ring 310 components), height, and/or strut shape, a support structure 300 can be constructed having specific physical properties. For example, a support structure 300 can be constructed that has a specific high push force, while also maintaining particular requirements for softness, flexibility, and radial expansion.

Figure 8:
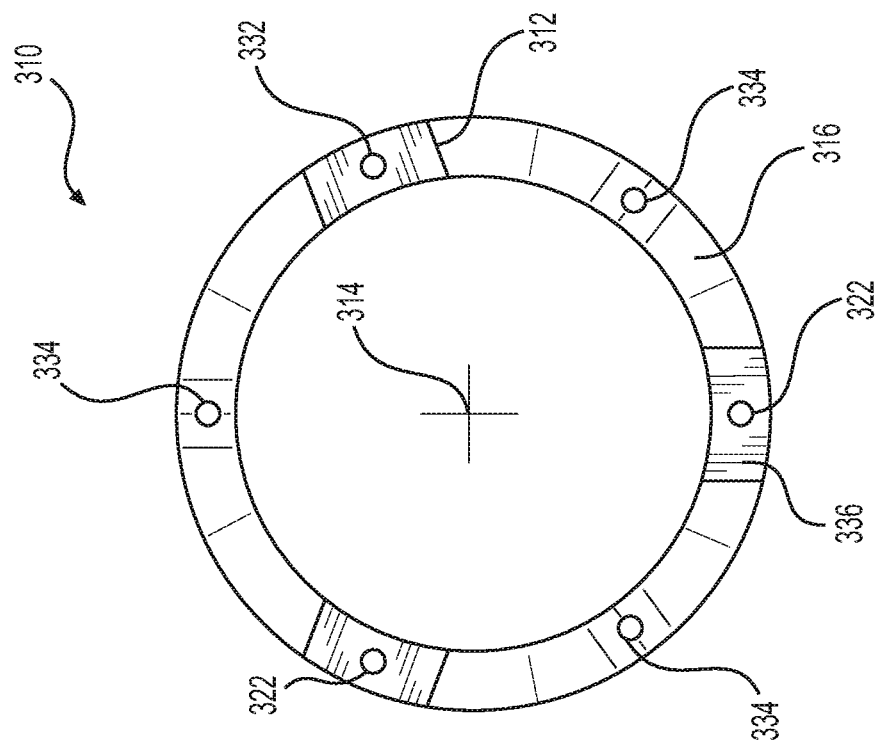
FIG. 8 is a top view of the expandable ring of FIG. 5.
Figure 7:
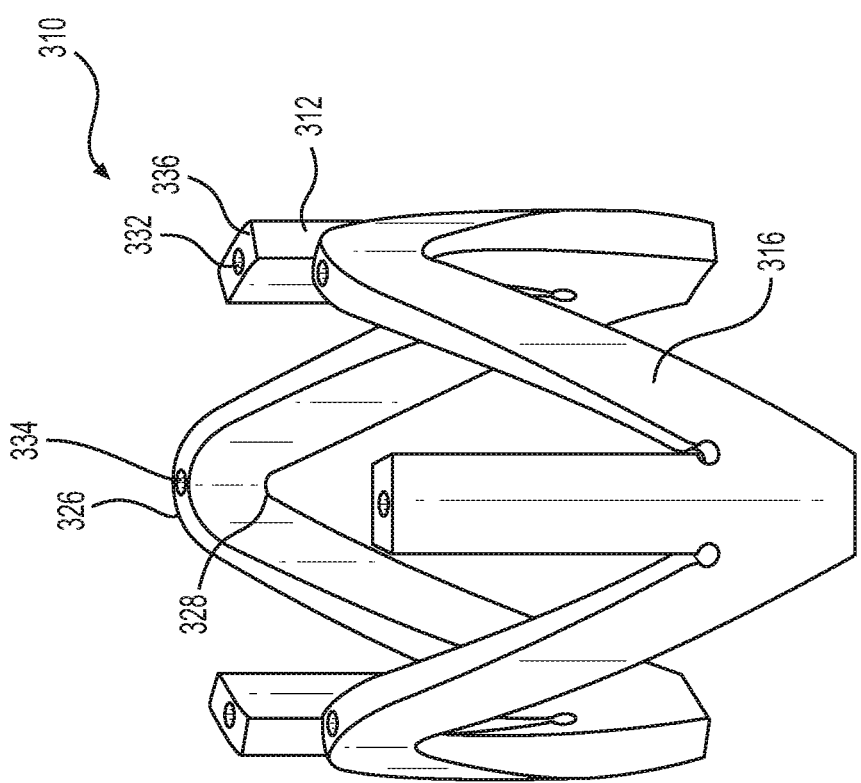
FIG. 7 is a perspective view of the expandable ring of FIG. 5.

FIGS. 7 and 8 provide a top view of the expandable ring 310. As described above, a coupling member 320 extends through each of the expandable rings 310 and longitudinally couples the individual rings 310 along the support structure 300. During assembly, the rings 310 are axially aligned such that the corresponding throughbores 332, 334 of adjacent rings align. The coupling member 320 extends through the throughbores 332, 334 and secures the axial/longitudinal and rotational position of the expandable rings 310 along the support structure 300.

As provided in FIGS. 7 and 8, the beams 312 and/or struts 316 can include a throughbore 332, 334 for receiving the coupling member 320. On the beams 312, the throughbore 332 extends longitudinally and in a straight line from the top surface 336 through the bottom surface 338 of the beam 312. Likewise, on the struts 316, the throughbore 334 extends longitudinally and in a straight line from the apex 326 of the strut 316, through the thickness of the strut 316, to the interior bend 328 defined between the two legs 322, 324. While FIGS. 7 and 8 illustrates a throughbore 332, 334 provided on each of the longitudinal beams 312 and each of the struts 316, it is not necessary that each beam 312 and strut 316 include a throughbore 332, 334 connected via individual coupling members 320. In some embodiments, only one coupling member 320 extends through a single beam 312 or a single strut 316 to couple the series of expandable rings 310 comprising the support structure 300.

The throughbore 332, 334 can have a smooth surface or a textured surface. In some embodiments, the throughbore 332, 334 can include threads for engaging with corresponding threads provided on the coupling member 320. The throughbore 332, 334 can have a constant or varying diameter along the length of the expandable ring 310. It also contemplated that various rings 310 along the length of the support structure 300 can include throughbores 332, 334 having various surface finish/texture, threads, and/or diameter. By varying the surface structure and/or size of the throughbore 332, 334, the coupling between the ring 310/throughbore 332, 334 and the coupling member 320 can be controlled. For example, by constructing the coupling member 320 with a size and/or shape corresponding to the size/shape of the throughbore 332, 334, longitudinal and rotational movement of the ring 310 with respect to the coupling member 320 can be prohibited or otherwise limited. In on example, the throughbore 332, 334 can include a groove or recess provided on its interior surface that is sized and shaped to correspond to a projection extending from the coupling member 320 such that rotation of the ring 310 on the coupling member 320 is prevented or limited. Likewise, the throughbore 332, 334 can include a thread or reduced diameter portion that interferes/contacts a corresponding portion of coupling member 320 to fix longitudinal and rotational the position of the ring 310 along/about the coupling member 320.

The longitudinal beams 312 and/or struts 316 can also include a mating feature (not shown) sized and configured to couple with a corresponding feature provided on an adjacent ring 310. For example, the top surface 336 of a beam 312 can include a projection sized and located to engage a corresponding recess provided on the bottom surface 338 of the adjacent beam 312. The mating feature can be included on a single beam 312 or on all the beams 312 of the ring 310. In an example embodiment, one beam 312 of each of the rings 310 included on the support structure 300 includes mating features. In another example, all the beams 312 include a mating feature and the coupling member 320 extends through a strut 316 as described above.

Figure 9:
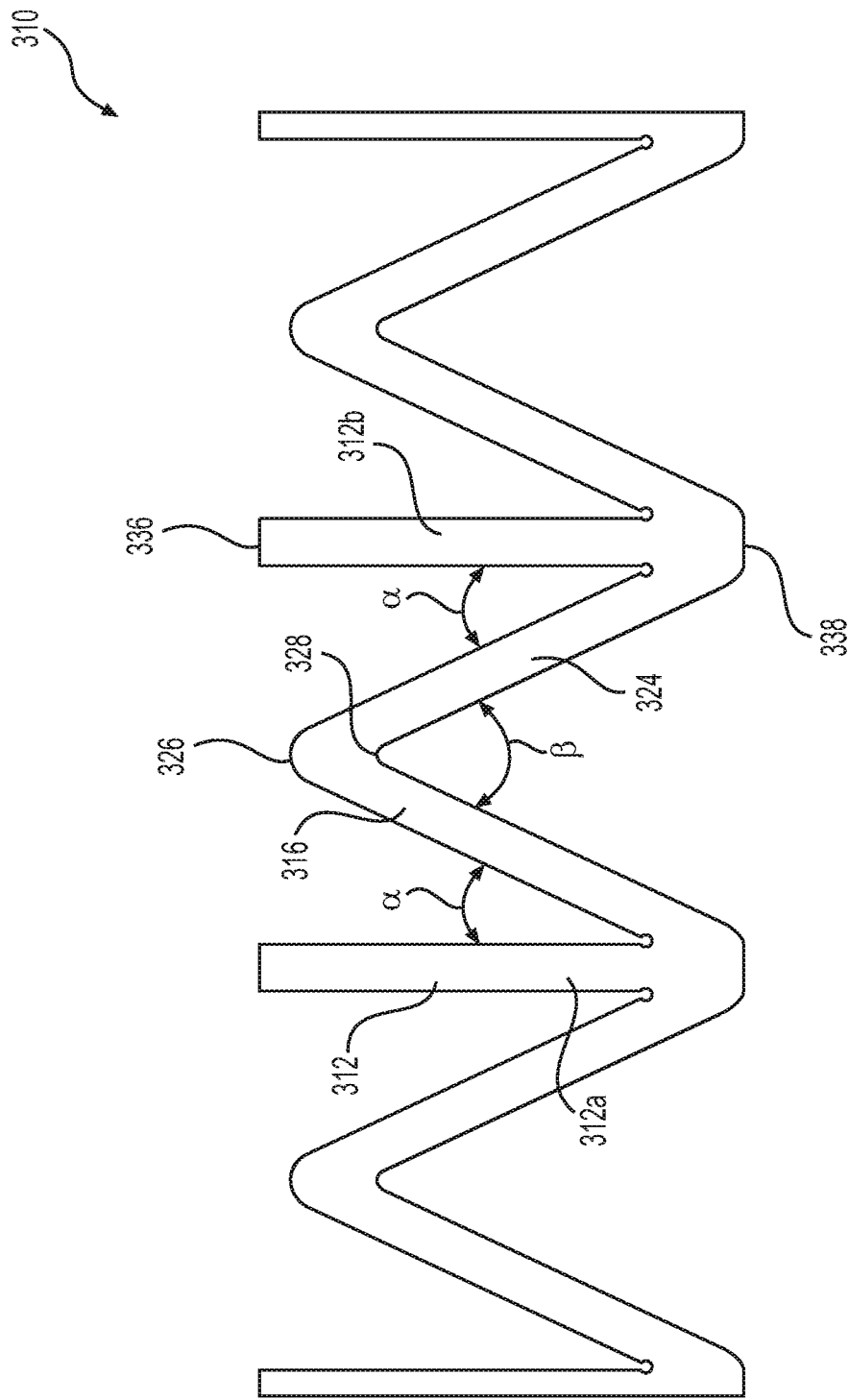
FIG. 9 is a flattened view of the expandable ring of FIG. 5.

Further illustrating the relationship between the struts 316 and beams 312, FIG. 9 illustrates the unexpanded expandable ring 310 cut along a longitudinal beam 312 and laid flat. The expandable rings 310 can be manufactured by creating the form illustrated in FIG. 9 and joining opposing sides of the ring 310 together. For example, the structure provided in FIG. 9 can be formed by injection molding or laser cutting a piece of material, and welded or otherwise fixedly joined together the opposing ends of the ring 310 along the beam 312. The ring 310 can also be manufactured by laser cutting or mechanically cutting the beams 312 and struts 316 from a cylindrical or tubular piece of material.

Figure 11:
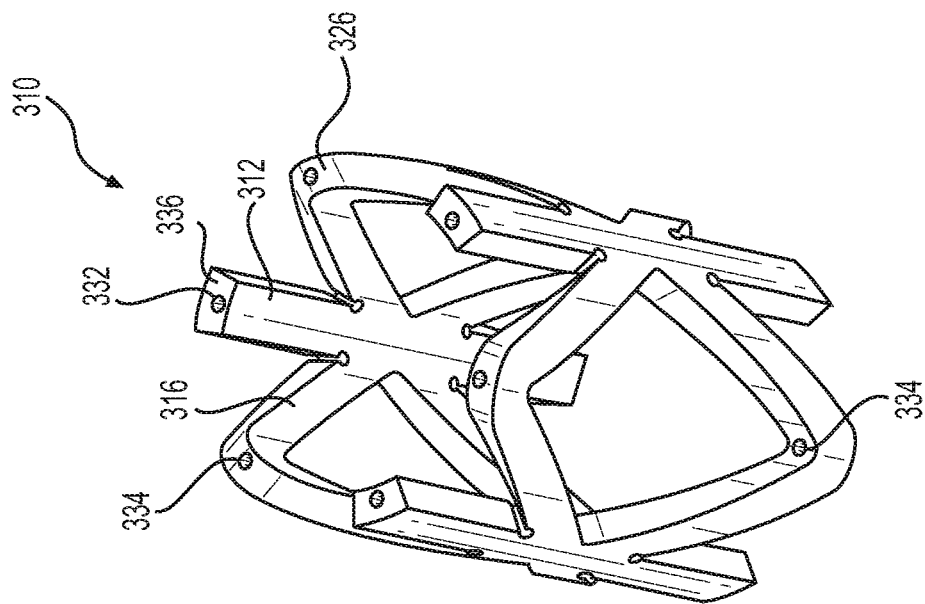
FIG. 11 is a perspective view of the expandable ring of FIG. 10.
Figure 10:
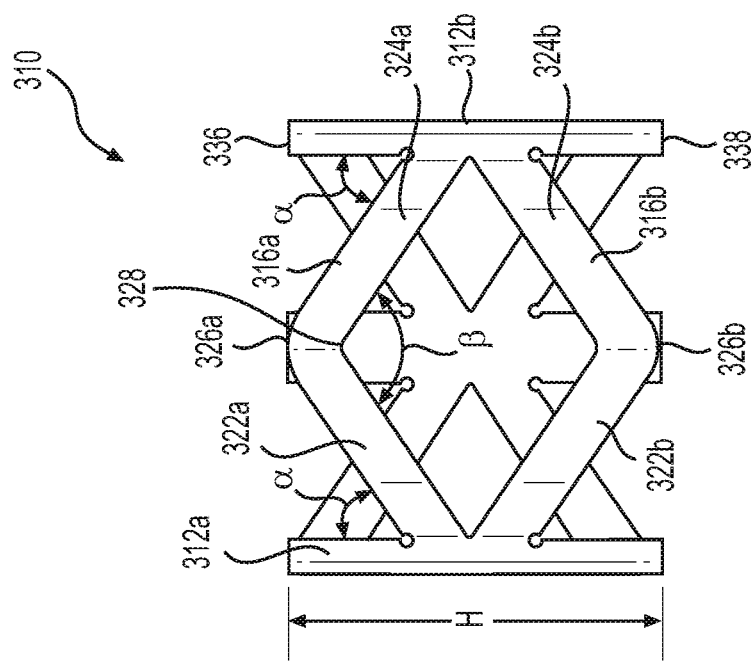
FIG. 10 is a front view of an example expandable ring.

FIGS. 10 and 11 provide side and perspective views of an example expandable ring 310 having an alternate strut 316 configuration. The expandable ring 310 of FIGS. 10 and 11 have similar components, operation, and are manufactured by similar methods as the expandable ring 310 of FIGS. 3-9. Accordingly, only the differences between the expandable ring 310 of FIGS. 10 and 11 will be described below. Like reference numbers are used to indicate like elements.

The expandable ring 310 depicted in FIGS. 10 and 11 can be coupled in series with additional expandable rings 310 (of similar or varying design) and be axially aligned along the longitudinal axis of the inner tubular member 130/sheath 120 to form an elongated tubular support structure 300. As illustrated in FIGS. 10 and 11, the expandable ring 310 includes an upper and lower strut 316a, 316b extending between adjacent beams 312a, 312b. The upper and lower struts 316a, 316b each define a generally "V" shape and a generally diamond shape in combination. The upper strut 316a includes a first leg 322a and a second leg 324a that extend at acute angles ($\alpha$) from the midpoint of the adjacent beams 312a and 312b towards the top surface 336 of the ring 310/beams 312. The first and second legs 322a, 324a meet at an apex 326a such that an acute angle ($\beta$) is defined between the legs 322a, 324a. The lower strut 316b includes a first leg 322b and a second leg 324b that extend at acute angles ($\alpha$) from the midpoint of the adjacent beams 312a and 312b towards the bottom surface 338 of the ring 310/beams 312. The first and second legs 322b, 324b meet at an apex 326b such that an acute angle ($\beta$) is defined between the legs 322b, 324b. As illustrated in FIG. 10, the apexes 326a, 326b of the upper and lower struts 316a, 316b, each have a height corresponding to the height (H) of the non-expanded ring 310. Similar to the expandable ring 310 depicted in FIGS. 5 and 6, as the ring 310 of FIGS. 10 and 11 expands, the upper and lower struts 316a and 316b will flex, move, and/or elongate circumferentially around the perimeter of the expanded ring 310 such that the angle ($\alpha$) and angle ($\beta$) increase, and the height of the apexes 326a, 326b of the upper and lower struts 316a, 316b will decrease. Once the prosthetic device/delivery apparatus 200 has passed through the expandable ring 310, and upper and lower struts 316a, 316b will return to their original, non-expanded configuration.

Figure 13:
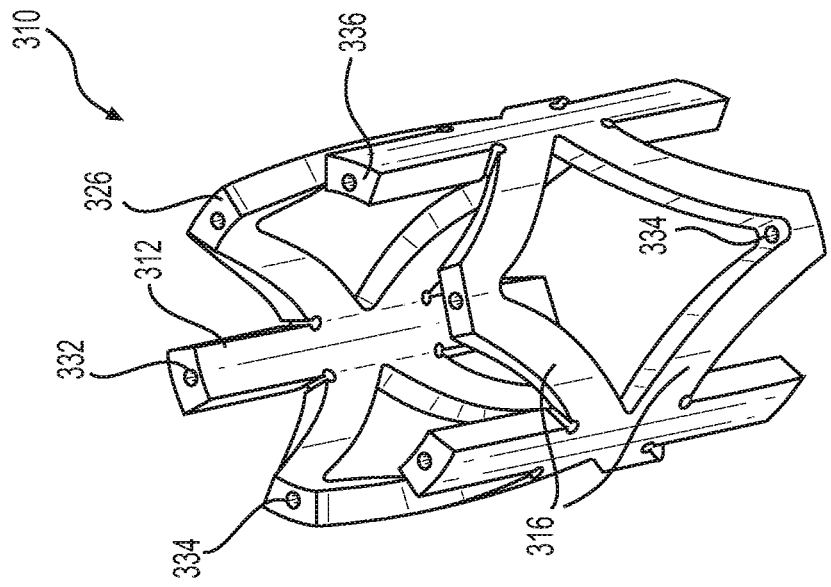
FIG. 13 is a perspective view of the expandable ring of FIG. 12.
Figure 12:
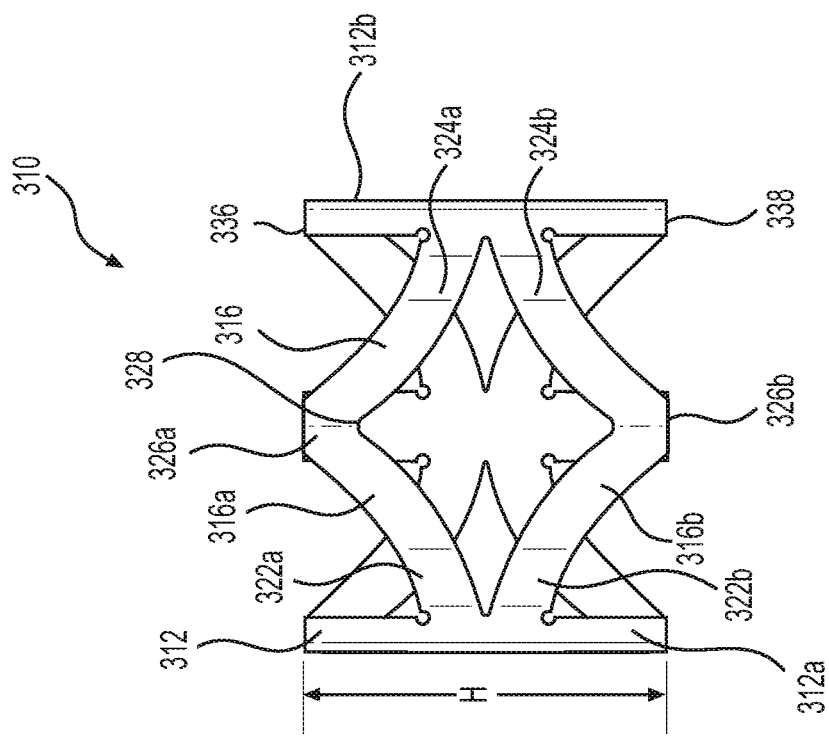
FIG. 12 is a front view of an example expandable ring.

FIGS. 12 and 13 provide side and perspective views of an example expandable ring 310 having an alternate strut 316 configuration. The expandable ring 310 of FIGS. 12 and 13 have similar components, operation, and are manufactured by similar methods as the expandable ring 310 of FIGS. 3-11. Accordingly, only the differences between the expandable ring 310 of FIGS. 12 and 13 will be described below. Like reference numbers are used to indicate like elements.

The expandable ring 310 depicted in FIGS. 12 and 13 can be coupled in series with additional expandable rings 310 (of similar or varying design) and axially aligned along the longitudinal axis of the inner tubular member 130/sheath 120 to form an elongated tubular support structure 300. As illustrated in FIGS. 12 and 13, the expandable ring 310 includes an upper and lower strut 316a, 316b extending between adjacent beams 312a, 312b. The upper and lower struts 316a, 316b each define a curved "V" shape. The upper strut 316a includes a first leg 322a and a second leg 324a having concave curved shape that extend from the midpoint of the adjacent beams 312a and 312b towards the top surface 336 of the ring 310/beams 312. Similarly, the lower strut 316b includes a first leg 322b and a second leg 324b having a concave shape the extend from the midpoint of the adjacent beams 312a and 312b towards the bottom surface 338 of the ring 310/beams 312. As illustrated in FIG. 11, the apexes 326a, 326b of the upper and lower struts 316a, 316b, each have a height corresponding to the height (H) of the non-expanded ring 310. Similar to the expandable ring 310 depicted in FIGS. 5 and 6, as the ring 310 of FIGS. 12 and 13 expands, the upper and lower struts 316a and 316b will flex, move, and/or elongate circumferentially around the perimeter of the expanded ring 310 such that curvature of the first leg 322a and the second leg 324a of the upper strut 316a, and the curvature of the first leg 322b and the second leg 324b of the lower strut 316b will decrease, and the height of the apexes 326a, 326b of the upper and lower struts 316a, 316b will decrease. Once the prosthetic device/delivery apparatus 200 has passed through the expandable ring 310, and upper and lower struts 316a, 316b will return to their original, non-expanded configuration.

Figure 15:
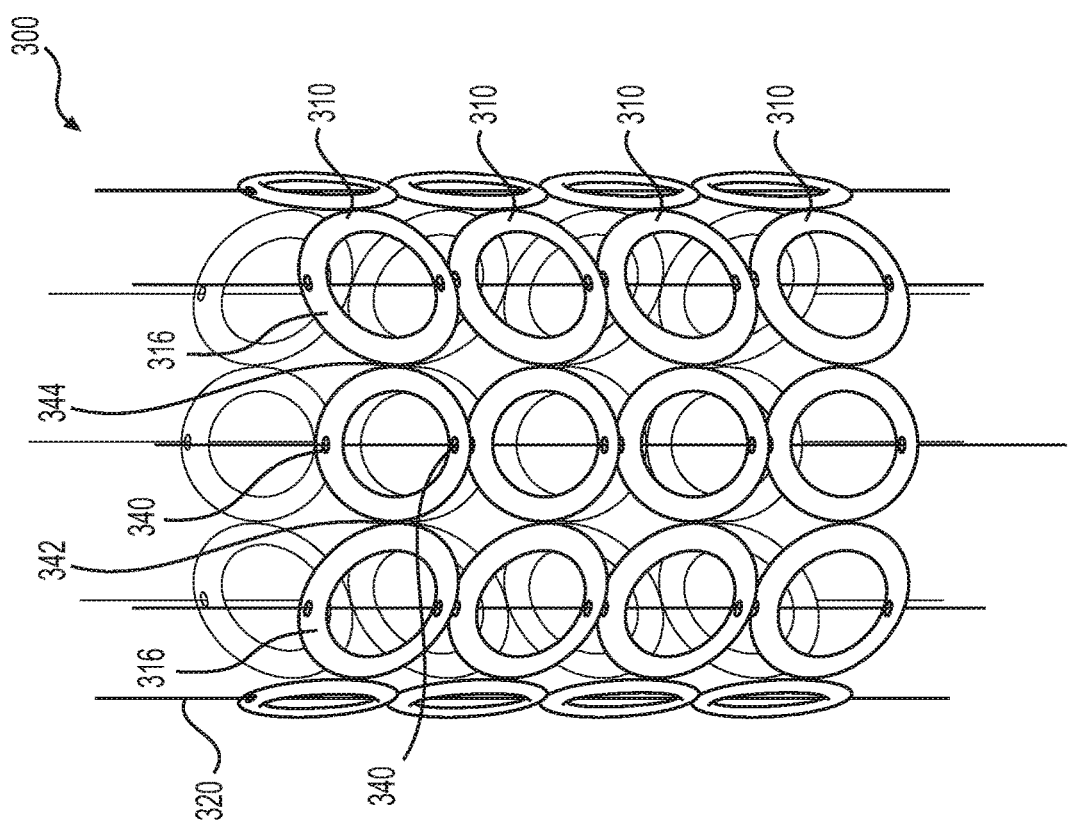
FIG. 15 is a perspective view of the expandable ring of FIG. 14.
Figure 14:
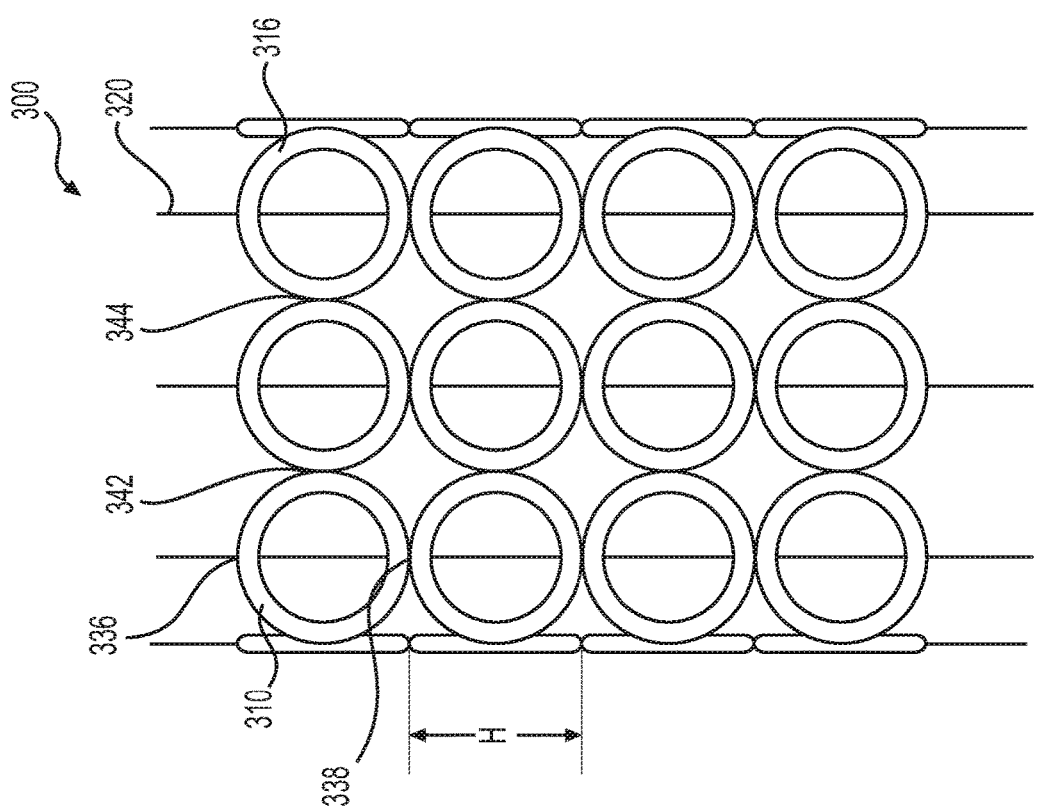
FIG. 14 is a front view of an example expandable ring.

FIGS. 14 and 15 provide side and perspective views of an example support structure 300. The support structure 300 includes several radially expandable rings 310 coupled together and axially aligned along the longitudinal axis of the inner tubular member 130/sheath 120 to form an elongated tubular structure. The expandable rings 310 of FIGS. 14 and 15 have similar components, operation, and are manufactured by similar methods as the expandable ring 310 of FIGS. 3-13. Accordingly, only the differences between the expandable rings 310 of FIG. 14 will be described below. Like reference numbers are used to indicate like elements. As illustrated in FIGS. 14 and 15, each of the expandable rings 310 includes several ring-shaped struts 316 spaced around the circumference of the expandable ring 310. The struts 316 can define a torus shape or a circular/ring shape with generally flat and parallel outer and inner surfaces. Adjacent struts 316 are coupled at a location on the perimeter of the ring-shaped strut 316. As provided in FIGS. 14 and 15, ring-shaped struts 316 can be coupled at opposing points on the perimeter of the strut 316. For example, a first coupling point 342 can be located at a first position on the perimeter of the strut 316, and a second coupling point 344 can be located at a position 180-degrees around the perimeter of the strut 316. At least one coupling member 320 is used to join adjacent rings 310 and to maintain the axial/longitudinal position of the expandable rings 310 along the support structure 300 and inner tubular member 130. The ring-shaped struts 316 include a throughbore 340 for receiving a coupling member 320. The throughbore 340 extends through the ring-shaped strut 316 at the edge adjacent the top surface 336 of the ring 310 and through the edge adjacent the bottom surface 338 of the ring 310. During expansion of the support structure 300, the individual ring-shaped struts 316 deform/flex as the diameter of the expandable ring 310 increases. As outlined above, in the non-expanded state, the ring-shaped struts 316 have a generally circular shape. In an expanded state, the ring-shaped struts 316 change shape as the diameter/circumference of the expandable ring 310 increases. For example, as the expandable ring 310 expands the ring-shaped struts 316 elastically deform to have a generally elliptical or oval shape where the height (H) of the ring-shaped struts 316 decreases as the expandable ring 310 expands.

In another embodiment shown in FIGS. 16-21, the support structure 300 comprises a number of interconnected radial members 350 circumferentially arranged to define the tubular form of the support structure 300/inner tubular member 130/sheath 120. Each of the elongated radial members 350 are slidably connected to an adjacent radial member 350 to facilitate expansion of the support structure 300. The slidable connection between adjacent radial members 350 accommodates passage of the delivery apparatus 200 and delivery of the prosthetic device through the central lumen 330 of the support structure 300. Like the support structure 300 of FIGS. 3-15, a lubricious liner can be provided within the central lumen 330 to reduce friction between the passing delivery apparatus 200/prosthetic device and support structure 300.

Figure 17:
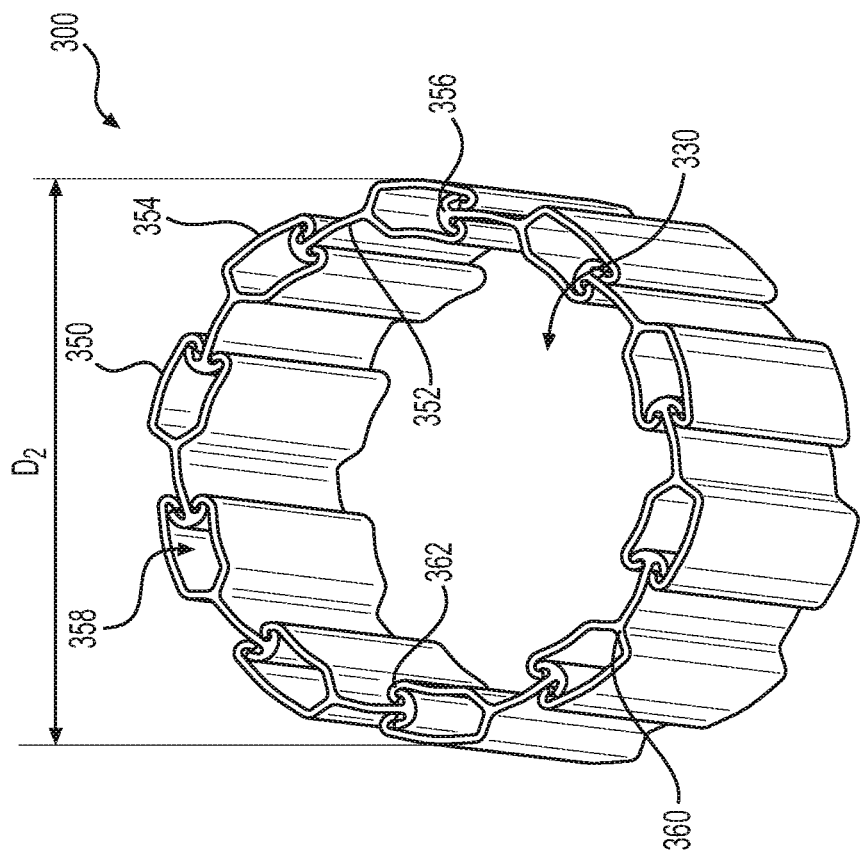
FIG. 17 is a top perspective view of the support structure of FIG. 16 in an expanded configuration.
Figure 16:
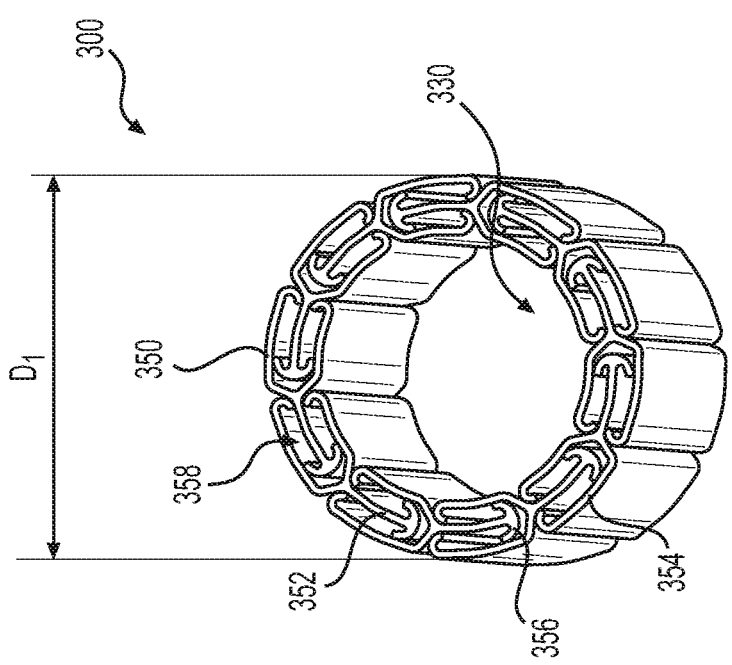
FIG. 16 is a top perspective view of an example expandable support structure in a non-expanded configuration.

FIGS. 16 and 17 provides a top perspective of an example expandable support structure 300. FIG. 16 illustrates the support structure 300 in a non-expanded state and FIG. 17 illustrates the support structure in an expanded state. To the extent that there are similarities between the support structure 300 of FIGS. 3-15, like reference numbers are used to indicate like elements.

As provided in FIGS. 16 and 17, the support structure 300 includes a number of elongated radial members 350. Each of the radial members 350 forms an elongated structure that will extend along a length of the inner tubular member 130. Each radial member 350 includes a locking arm 352 and a retaining portion 354. As illustrated in FIGS. 15 and 16, the radial members 350 are circumferentially arranged around the support structure 300 such that the locking arm 352 of each of the radial members 350 slidably engages the corresponding retaining portion 354 of an adjacent radial member 350. A locking projection 356 extends from the end of the locking arm 352. When coupled, the locking projection 356 and the locking arm 352 extend into the channel 358 included in the retaining portion 354 of an adjacent radial member 350. The locking projection 356 and locking arm 352 are sized and configured to slide freely within the channel 358.

The radial members 350 move circumferentially to expand the support structure 300 radially between a non-expanded and expanded state, thereby facilitating radial expansion of the inner tubular member 130/sheath 120 while maintaining the overall length of the support structure 300. As illustrated in FIGS. 16 and 17, the locking arm 352/locking projection 356 moves/slides in a direction around the circumference of the support structure 300 within the channel 358 of the retaining portion 354. As the locking arm 352/locking projection 356 move from a first position adjacent the end 360 of the channel 358 towards the opening 362 provided in the retaining portion 354, the circumference/diameter of the support structure 300 increases. As provided in FIGS. 16 and 17, the expanded diameter ($D_2$) (and circumference) of the support structure 300 is greater than the non-expanded diameter ($D_1$) (and circumference) of the support structure 300. It is also contemplated that the locking arm 352 can slide axially within the channel 358 of an adjacent radial member 350. For example, during assembly, each of the radial members 350 may be constructed individually and assembled by sliding the locking arm 352 of a first radial member 350 into the channel 358/retaining portion 345 of an adjacent radial member 350 until the tubular form of the support structure 300 is constructed. As will be discussed in more detail below, locking arms 352 may also be forced through the openings 362 and into the retaining portion 354 of an adjacent radial member 350.

While FIGS. 16 and 17 illustrate a support structure 300 including ten radial members 350, it is contemplated that additional or fewer radial members 350 can be included depending on the desired size, flexibility, and expansion properties of the support structure 300. The length of the elongated radial members 350 can correspond to the length of the inner tubular member 130 such that the support structure 300 extends the entire length of the inner tubular member 130. In another embodiment, the elongated radial members 350 extend along a majority of the entire length of the inner tubular member 130 and can be positioned along/coupled to any portion of the length of the inner tubular member 130. In a further embodiment, the elongated radial members 350 extend along a minority of the entire length of the inner tubular member 130 and can be positioned along/coupled to any portion of the length of the inner tubular member 130. In another embodiment, the inner tubular member 130 can include several support structures 300 (comprising slidably interconnected radial members 350) axially aligned along the longitudinal axis of the inner tubular member 130. The support structures 300 can be spaced apart along the inner tubular member 130 or positioned immediately adjacent/abutting. The support structures 300 can be coupled via a coupling member 320 extending through each of the support structures 300. The adjacent support structures 300 can have varying length and spacing along the length of the inner tubular member 130. For example, a first support structure 300 can have a length, for example a length of about 10.0 mm. A second support 300 provided along the inner tubular member 130 can be shorter than the first support structure 300, for example 5.0 mm. A third support structure provided along the inner tubular member 130 can be shorter than the second support structure 300, for example, 2.5 mm. By providing a series of support structures 300 having varying length (and spacing) along the inner tubular member 130, the flexibility of the inner tubular member 130/sheath 120 can be improved and controlled.

In a further embodiment, the inner tubular member 130 can include a combination of support structures 300 (comprising slidably interconnected radial members 350) and expandable rings 310 axially aligned along a longitudinal axis of the inner tubular member 130. The adjacent support structures 300 and expandable rings 310 can be spaced apart along the inner tubular member 130 or positioned immediately adjacent/abutting. The adjacent support structures 300 and expandable rings 310 can be coupled via a coupling member 320 extending through each of the support structures 300 and expandable rings 310.

Figure 18:
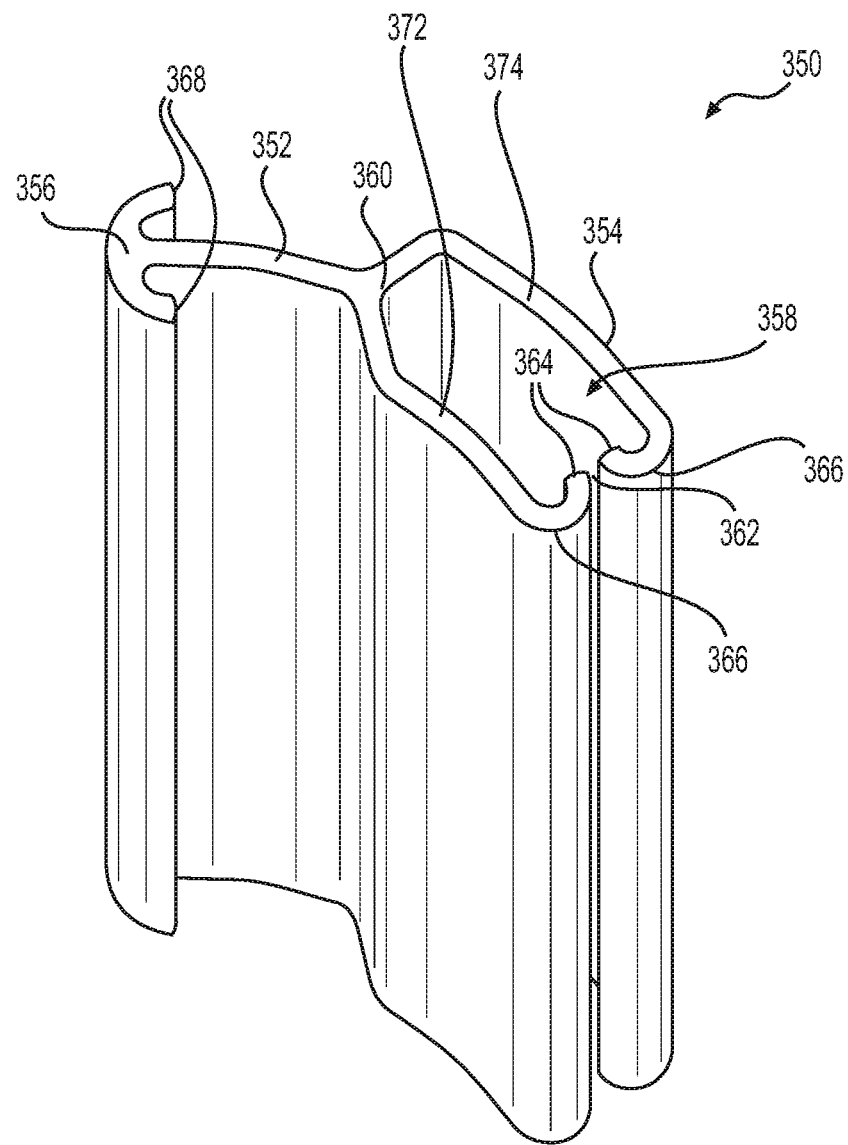
FIG. 18 is a top perspective view of an element of the support structure of FIG. 16.

FIG. 18 illustrates a single radial member 350. The radial member 350 defines an arcuate shape in cross-section, having a curvature corresponding to the curvature/radius of the expanded and non-expanded support structure 300 and/or inner tubular member 130. The elongated retaining portion 354 includes a curved internal wall 372 and a correspondingly-shaped curved external wall 374. The wall thickness of the support structure 300 is defined by the thickness of the retaining portion 354 between the curved internal wall 372 and the curved external wall 374. In an example support structure 300, the wall thickness is about 0.65 mm (2F). The internal and external walls 372, 374 are spaced apart such that the hollow channel 358 is provided therebetween. The channel 358 has an opening sufficient to allow free circumferential movement of the locking arm 352 and locking projection 356 of an adjacent radial member 350. An end 360 of the channel 358 provides a contact surface for limiting movement of the locking projection 356/locking arm 352. In one example, the end 360 of the channel 358 can have a size and shape corresponding to the size and shape of the locking projection 356. In another example (not shown), the end 360 of the channel 358 can have an engagement feature for engaging the locking projection 356 to releasably engage the locking projection 356 within the channel 358 and maintain the support structure 300 in a non-expanded configuration. Opposite the end 360 is the entrance opening 362 to the channel 358/retaining portion 354. The entrance opening 362 can be sized and configured to slidably receive the locking arm 352 of an adjacent radial member 350. The retaining portion 354 can include an engagement member 364 at the opening 362 for retaining the locking projection 356 within the channel 358. As illustrated in FIG. 18, the engagement member 364 includes a curved inwardly projecting surface that extends from the end surface 366 of the retaining portion 354, at the opening 362, towards and into the channel 358. The engagement member 364 is provided such that the locking projection 356 of an adjacent radial member 350 cannot be removed from the retaining portion 354 without fatally deforming and/or damaging either the locking arm 352 or the retaining portion 354.

Figure 19:
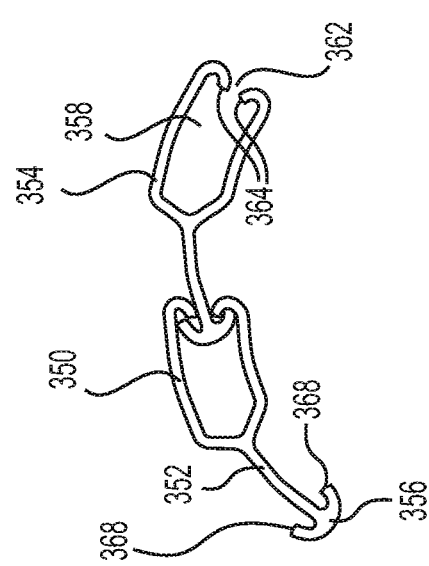
FIG. 19 is a top view of the element of FIG. 18.

As provided in FIGS. 18 and 19, the locking arm 352 extends from the retaining portion 354 in a circumferential direction opposite the opening 362. The locking projection 356 extends from the end of the locking arm 352 and is sized and configured circumferentially slide within the channel 358 of an adjacent radial member 350. The locking projection 356 illustrated in FIG. 18 defines a generally U-shape in cross section. As will be described below in reference FIGS. 19-21, different shaped locking projections 356 and engagement members 364 are contemplated. For example, the locking projection 356 can have a U-shape, a V-shape, a T-shape, a W-shape, or any other regular or irregular shape that will maintain the locking projection 356 within the channel 358 of the retaining portion 354. As illustrated in FIG. 18, the locking projection 356 defines a U-shape in cross-section that includes two contact surfaces for 368 for engaging the engagement member 364 of the retaining portion 354.

Figure 21:
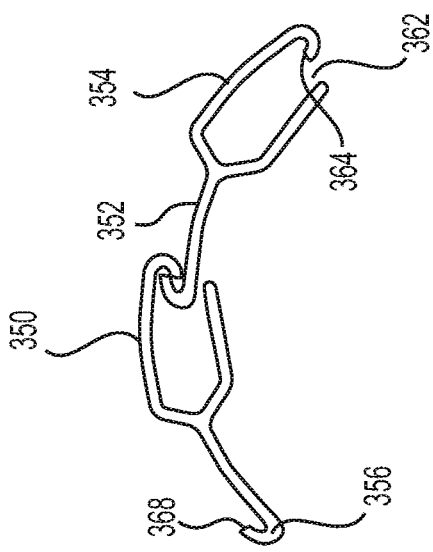
FIG. 21 is a top view of an example element for an expandable support structure.
Figure 20:
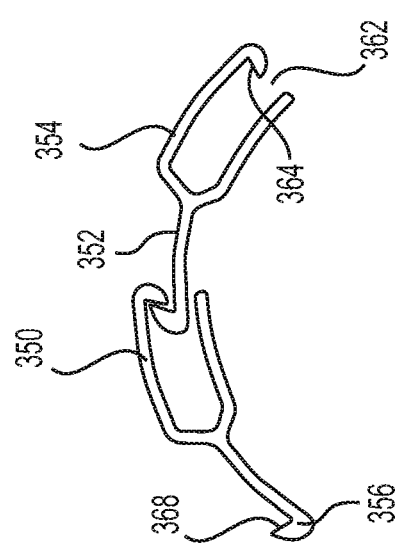
FIG. 20 is a top view of an example element for an expandable support structure.

FIGS. 20 and 21 illustrate hook-type structures for the locking projection 356 and the corresponding engagement member 364/opening 362. As illustrated in FIG. 20, a hook-shaped (or J-shaped) locking projection 356 extends from the end of the locking arm 352. The locking projection 356 includes a flat and angled contact surface 368 for engaging the engagement member 364 of the retaining portion 354. The engagement member 364 includes a correspondingly shaped, flat and angled surface such that contact between the two maintains the locking arm 352 within the retaining portion 354. Likewise, the opening 362 is sized to allow one-way/inward movement of the locking arm 352 into the channel 358 of the retaining portion 354. FIG. 21 also illustrates a hook-shaped (or J-shaped) locking projection 356 extending from the end of the locking arm 352. The locking projection 356 includes curved contact surface 368 for engaging the engagement member 364 of the retaining portion 354. The engagement member 364 includes a correspondingly shaped curved portion defining a bowl/recessed sized to receive the contact surface 368 of the locking projection 356 such that engagement between the two maintains the locking arm 352 within the retaining portion 354. Likewise, the opening 362 is sized to allow one-way/inward movement of the locking arm 352 into the channel 358 of the retaining portion 354.

Similar to the support structures 300 illustrated in FIGS. 3-15, the example support structure 300 and radial members 350 provided in FIGS. 16-21 can be formed by injection molding or laser cutting a piece of material. The support structure 300 and radial members 350 provided in FIGS. 16-21 can also be formed by extruding. Adjacent radial members 350 can be coupled by pushing or otherwise forcing the locking projection 356 through the opening 362 and into the channel 358 of an adjacent radial member 350. It is also contemplated that the locking arm 352 can then be slidingly coupled to the retaining portion 354 of an adjacent radial member 350 by sliding the locking projection 356 from the (open) end of the support structure 300 axially through the channel 358. It is also contemplated that adjacent radial members 350 can be formed by co-extruding at least two radial members 350 in a coupled configuration. The assembled support structure 300 of FIGS. 16-21 can be covered with an elastic coating. The assembled support structure 300 can also be coupled to an inner or outer surface of the inner tubular member 130 or encased within the inner tubular member 130. The elastic outer tubular member 150 can be provided over the inner tubular layer 130, where the outer tubular layer 150 comprises a material having an elastic modulus greater than an elastic modulus of the inner tubular layer 130.

As described above, the sheath 120 of the present disclosure can be used with various methods of introducing a prosthetic device, such as a transcatheter heart valve, into a patient's vasculature. For example, the sheath 120 can be used to deliver, remove, repair, and/or replace a prosthetic device. Generally, during use, the expandable sheath 120 is passed through the skin of patient (over a guidewire, in some embodiments) such that the distal end region of the sheath 120 is inserted into a vessel, such as a femoral artery, and then advanced to a wider vessel, such as the abdominal aorta. A heart valve prosthetic device (in a crimped state) can be placed on the distal end portion of the delivery apparatus 200 around the balloon 240. The delivery apparatus 200 is then inserted through the expandable sheath 120 and the prosthetic device, and the prosthetic device is delivered to the treatment site where it is implanted within the patient.

The balloon 240 and prosthetic device are inserted through the central lumen 330 of support structure 300 (and the inner tubular member 130). The prosthetic device and the delivery apparatus 200 exert a radially outwardly directed force on the adjacent portion(s) of the support structure 300. The support structure 300 exerts a corresponding radially outward directed force on the inner tubular member 130 which exerts a corresponding radially outwardly directed force on the elastic outer tubular member 150, causing both the inner and outer tubular members 130, 150 to locally expand to accommodate the profile of the prosthetic device. As described above with respect to FIGS. 3-15, as the expandable rings 310 (individually) expand the struts 316 expand circumferentially such that the distance between adjacent beam 312 increases, increasing the diameter of the central lumen 330 of the support structure 300. The struts 316 temporarily change shape under the force of the passing prosthetic device/delivery apparatus 200 and return to their original shape once the device/apparatus 200 has passed. As described above with respect to FIGS. 16-21, interconnected radial members 350 slide/move circumferentially with respect to each other between an expanded and non-expanded configuration. The locking arm 352 of each radial member 350 slides circumferentially within the channel 358 provided in an adjacent radial member 350 to increase the overall diameter/circumference of the central lumen 330 of the support structure 300. In both embodiments, as the prosthetic device passes, the support structure 300 returns to the non-expanded configuration. Likewise, the sheath 120, including the inner and outer tubular layers 130, 150 return to their original, non-expanded configuration. In some embodiments, this is facilitated by the outer tubular member 150 having a higher elastic modulus than inner tubular member 130. In this configuration, the outer tubular member 150 urges the inner tubular member 130 back towards its non-expanded configuration.

After the distal end of the delivery apparatus 200 and the balloon 240 have passed passing through the distal opening of the sheath 120, the prosthetic device 250 is positioned at the treatment site and the balloon 240 expanded to deploy the prosthetic device. The prosthetic device is then transitioned from the original crimped configuration on the unexpanded balloon 240, to an expanded/deployed configuration on the expanded balloon 240. Once the balloon 240 is expanded and the prosthetic device positioned at the treatment site, the balloon 240 is then deflated and withdrawn through the sheath 120.

As described above, expansion and recovery of the inner and outer tubular members 130, 150 can be controlled by providing an outer tubular member 150 comprised of a material having a higher elastic modulus than the inner tubular member 130. As a result, the outer tubular member 150 urges the inner tubular member 130 back towards a non-expanded configuration. The inner tubular member 130 can also comprise a more lubricious material and/or coating compared to the outer tubular member 150. For example, the outer tubular member 150 can be made of, or incorporate, polyurethane, silicone, and/or rubber. The outer tubular member 150 and the inner tubular member 130 can be made of, or incorporate, for example, PTFE (e.g. Teflon®), polyimide, PEEK, polyurethane, nylon, polyethylene, polyamide, polyether block amides (e.g. PEBAX®), polyether block ester copolymer, polyesters, fluoropolymers, polyvinyl chloride, thermoset silicone, latex, polyisoprene rubbers, polyolefin, other medical grade polymers, or combinations thereof. It is also contemplated that the outer tubular member 150 and the inner tubular member 130 can include a shape memory alloy such as Nitinol, and/or stainless steel, cobalt chromium, spectra fiber, polyethylene fiber, aramid fiber, or combinations thereof.

Beyond transcatheter heart valves, the introducer sheath system 100 described herein can be useful for other types of minimally invasive surgery, such as any surgery requiring introduction of an apparatus into a subject's vessel. For example, the expandable sheath 120 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. An expandable sheath for delivering a prosthetic device comprising:
   at least two expandable rings, including:

longitudinally extending beams spaced circumferentially around each expandable ring of the at least two expandable rings;

wherein at least one of the beams on each expandable ring of the at least two expandable rings includes a throughbore extending longitudinally through the beam;

an expandable strut extending between each of the beams;

the at least two expandable rings aligned along a longitudinal axis of the sheath and coupled together along a coupling member passing through each of the at least two expandable rings to form an elongated tubular structure;

wherein the coupling member extends through the throughbore;

wherein the at least two expandable rings expand radially between a non-expanded and expanded state.

2. The expandable sheath of claim 1, wherein each expandable ring of the at least two expandable rings have a height (H) between 2 mm and 20 mm measured along the longitudinal axis of the sheath.

3. The expandable sheath of claim 1, wherein the beams of each expandable ring of the at least two expandable rings include a throughbore, wherein a coupling member extends through each of the throughbores.

4. The expandable sheath of claim 1, wherein the coupling member includes at least one of a wire, a braided cable, and a polymer suture.

5. The expandable sheath of claim 1, wherein one of the beams on each expandable ring of the at least two expandable rings includes a proximal end mating feature at a proximal end of the beam and a distal end mating feature at a distal end of the beam, wherein the proximal end mating feature is sized and configured to engage the corresponding distal end mating feature of a longitudinally adjacent beam.

6. The expandable sheath of claim 1, wherein the beams on each expandable ring of the at least two expandable rings include a proximal end mating feature at a proximal end of the beam and a corresponding distal end mating feature at a distal end of the beam, wherein the proximal end mating features are sized and configured to engage the corresponding distal end mating features of longitudinally adjacent beams.

7. The expandable sheath of claim 1, wherein the expandable strut on each expandable ring of the at least two expandable rings expands circumferentially between the non-expanded and the expanded state such that a circumferential distance between adjacent beams of the corresponding ring increases during expansion, wherein the expandable strut on each expandable ring of the at least two expandable rings elastically deforms during expansion.

8. The expandable sheath of claim 1, wherein one of the expandable rings of the at least two expandable rings is constructed from a material having a stiffness greater than a stiffness of another one of the expandable rings.

9. The expandable sheath of claim 1, wherein, in the non-expanded state, the expandable strut on each expandable ring of the at least two expandable rings is coupled to the corresponding longitudinally extending beam at an acute angle and defines a generally "V" shape.

10. The expandable sheath of claim 1, wherein an overall length of the elongated tubular structure remains constant between the expanded and the non-expanded state.

11. The expandable sheath of claim 1, wherein the at least two expandable rings are coupled to an expandable inner tubular member, wherein an elastic outer member extends over the inner tubular member, and when the inner tubular member is in an expanded configuration, the elastic outer member urges the inner tubular member toward a non-expanded configuration.

12. The expandable sheath of claim 1, wherein the at least two expandable rings are encased within an expandable material, wherein an elastic outer member extends over the encased expandable rings, and when the expandable material is in an expanded configuration, the elastic outer member urges the expandable material toward a non-expanded configuration.

13. The expandable sheath of claim 1, wherein applying tension to the coupling member maintains the at least two expandable rings in an abutting configuration.

* * * * *